（12）United States Patent
Zhong (10) Patent No.: US 11,996,602 B1
(45) Date of Patent: May 28, 2024

(54) DETECTOR WITH DETACHABLE ANTENNA AND DETECTOR ASSEMBLY

(71) Applicant: Qianhua Zhong, Yichun (CN)

(72) Inventor: Qianhua Zhong, Yichun (CN)

(73) Assignee: Shenzhen Andelian Technology Co., Ltd., Guangdong (CN)

( * ) Notice: Subject to any disclaimer, the term of this patent is extended or adjusted under 35 U.S.C. 154(b) by 0 days.

(21) Appl. No.: 18/391,798

(22) Filed: Dec. 21, 2023

(51) Int. Cl.
*H01Q 1/08* (2006.01)
*H01Q 1/24* (2006.01)

(52) U.S. Cl.
CPC .............. *H01Q 1/088* (2013.01); *H01Q 1/242* (2013.01)

(58) Field of Classification Search
CPC ............................... H01Q 1/088; H01Q 1/242
See application file for complete search history.

(56) References Cited

U.S. PATENT DOCUMENTS

2011/0034140 A1\* 2/2011 Yanagi .................. H01Q 1/242
455/226.1

FOREIGN PATENT DOCUMENTS

JP 2016517296 A \* 6/2016 ............ A61B 90/00
KR 20080094555 A \* 10/2008

\* cited by examiner

*Primary Examiner* — Hoang V Nguyen (57) ABSTRACT

A detector with a detachable antenna includes detector body, a connecting piece, and an antenna. The detector body has a first connecting part, and the first connecting part is equipped with a signal receiving end. The first end of the connecting piece is detachably connected to the first connecting part. The antenna is provided with a second connecting part. The second connecting part is provided with a signal output end, and the second end of the connecting piece is detachably connected to the second connecting part to make the signal output end contact and electrically connected to the signal receiving end.

18 Claims, 8 Drawing Sheets

```
┌─────────────────────────┐
│   Pipeline endoscope    │
└─────────────────────────┘

┌─────────────────────────────────────┐
│ Detector with a detachable antenna  │
└─────────────────────────────────────┘
```

Figure 8

DETECTOR WITH DETACHABLE ANTENNA AND DETECTOR ASSEMBLY

BACKGROUND OF THE INVENTION

The present disclosure relates to the technical field of pipeline detection, in particular, to a detector with a detachable antenna and a detector assembly.

In people's daily lives, when it is necessary to detect pipelines, pipeline endoscope are often used. Pipeline endoscope can allow people to remotely view situation inside the pipeline without a need to disassemble or enter the pipeline, which is helpful for repairing, daily maintenance, and troubleshooting operations. When using pipeline endoscope to determine fault location, signal detectors are needed to detect a position of a probe of the pipeline endoscope, based on which, people can repair the fault.

At present, available detectors are all integrated, and an antenna cannot be removed from a detector body. However, such detectors have a long length, which is inconvenient to carry, and is prone to being damaged during movement and transportation.

Therefore, it is desired to provide a detector with a detachable antenna, which can effectively solve above problems, simple in structure, easy to disassemble and assemble, and convenient for use and transportation.

SUMMARY OF THE INVENTION

In order to overcome above technological problems, the present disclosure provides a detector with a detachable antenna and a detector assembly.

An embodiment of the present disclosure provides a detector with a detachable antenna. The detector with a detachable antenna includes detector body, a connecting piece, and an antenna. The detector body has a first connecting part, and the first connecting part is equipped with a signal receiving end. The first end of the connecting piece is detachably connected to the first connecting part. The antenna is provided with a second connecting part. The second connecting part is provided with a signal output end, and the second end of the connecting piece is detachably connected to the second connecting part to make the signal output end contact and electrically connected to the signal receiving end.

In at least one embodiment, the second connecting part comprises a sliding rod and an protruding structure protruding from a surface of the sliding rod, the connecting piece is provided with a sliding hole, an inner wall surrounding the sliding hole is provided with an blocking protrusion, and when the sliding rod is inserted into the sliding hole the protruding structure resists against the blocking protrusion.

In at least one embodiment, the detector with a detachable antenna further includes a sealing ring. The sealing ring is sleeved on the sliding rod and clamped between the protruding structure and the blocking protrusion.

In at least one embodiment, the connecting piece is provided with a connecting groove communicated with the sliding hole, and the first connecting part is configured to be inserted into the connecting groove to have the signal output end to contact and be electrically connected to the signal receiving end.

In at least one embodiment, an inner wall surrounding the connecting groove is provided with a first connecting thread, the first connecting part is provided with a second connecting thread, and the first connecting thread is configured to be threaded to the second connecting thread.

In at least one embodiment, the signal output end is provided with a first electrical contact of a concentric circular shape, the signal receiving end is provided with a second electrical contact corresponding to the first electrical contact, and the first electrical contact is configured to be electrically connected to the second electrical contact.

In at least one embodiment, a handle is provided on the detector body for a user to grip and use.

In at least one embodiment, the handle is provided with an uneven grip portion, which is used to fit the user's finger portion.

In at least one embodiment, a control board is provided inside the detector body, and the signal receiving end is electrically connected to the control board, and the control board receives a signal transmitted by the signal receiving end.

In at least one embodiment, a battery is provided inside the detector body, and the battery is electrically connected to and supplies power to the control board.

In at least one embodiment, a pointer meter is provided on an upper surface of the detector body and is electrically connected to the control board, the control board controls rotation of a pointer of the pointer meter based on the signal transmitted by the signal receiving end.

In at least one embodiment, an indicator light is provided on an upper surface of the detector body and is electrically connected to the battery, and the indicator light is configured to indicate remaining capacity of the battery.

In at least one embodiment, a switch is provided on a surface of the detector body and is electrically connected to the control board and configured to turn on or off the detector.

In at least one embodiment, the detector body is equipped with a sound playback device electrically connected to the control board, the control board controls the sound playback device to play sound based on the signal transmitted by the signal receiving end.

In at least one embodiment, an upper surface of the detector body is provided with a sound through-hole corresponding to the sound playback device.

In at least one embodiment, the detector with a detachable antenna further includes an adjustment switch electrically connected to the control board, and the adjustment switch is configured for the user to switch a signal frequency that the antenna can detect.

In at least one embodiment, the detector with a detachable antenna further includes a protective sleeve arranged at an end of the antenna.

Another embodiment of the present disclosure provides a detector assembly. The detector assembly includes a detector body, a connecting piece, and an antenna. The detector body has a first connecting part, and the first connecting part is equipped with a signal receiving end. The first end of the connecting piece is detachably connected to the first connecting part. The antenna is provided with a second connecting part. The second connecting part is provided with a signal output end, and the second end of the connecting piece is detachably connected to the second connecting part to make the signal output end contact and electrically connected to the signal receiving end.

The beneficial effect of the present disclosure is that, through arrangement of the above structures, the first and second connecting parts can be respectively connected through connecting pieces during use. At this time, the signal output end and the signal receiving end are in contact and electrically connected, making it convenient to connect the detector body and the antenna or to detach the antenna from the detector body, convenient to use, and convenient to store and carry.

BRIEF DESCRIPTION OF DRAWINGS

Implementations of the present disclosure will now be described, by way of embodiment, with reference to the attached figures. It should be understood, the drawings are shown for illustrative purpose only, for ordinary person skilled in the art, other drawings obtained from these drawings without paying creative labor by an ordinary person skilled in the art should be within scope of the present disclosure.

DETAILED DESCRIPTION OF THE INVENTION

It will be appreciated that for simplicity and clarity of illustration, where appropriate, reference numerals have been repeated among the different figures to indicate corresponding or analogous elements. In addition, numerous specific details are set forth in order to provide a thorough understanding of the exemplary embodiments described herein. However, it will be understood by those of ordinary skill in the art that the exemplary embodiments described herein may be practiced without these specific details. In other instances, methods, procedures, and components have not been described in detail so as not to obscure the related relevant feature being described. Also, the description is not to be considered as limiting the scope of the exemplary embodiments described herein. The drawings are not necessarily to scale and the proportions of certain parts may be exaggerated to better illustrate details and features of the present disclosure.

The term "comprising" when utilized, means "including, but not necessarily limited to"; it specifically indicates open-ended inclusion or membership in the so-described combination, group, series, and the like. The disclosure is illustrated by way of example and not by way of limitation in the figures of the accompanying drawings in which like references indicate similar elements. It should be noted that references to "an" or "one" embodiment in this disclosure are not necessarily to the same embodiment, and such references can mean "at least one". In addition, the terms "first" and "second" are used for descriptive purposes only and cannot be understood as indicating or implying relative importance or implying the number of indicated technical features. Thus, the features defined as "first" and "second" may explicitly or implicitly include one or more of the said features. In the description of embodiments of the application, "a plurality of" means two or more, unless otherwise specifically defined.

It should be noted that when a component is described as to be "fixed" on another component, it may be directly on said another component or may be fixed to said another component through an intermediate component. When one component is considered to be "connected" to another component, it may be connected directly to another component or may be connected to another component via an intermediate component. The terms "inside", "outside", "left", "right" and the like used herein are for purposes of illustration only and are not intended to represent the only embodiment.

Unless otherwise defined, all technical and scientific terms used in the present disclosure have the same meaning as those commonly understood by those skilled in the art. The terms used in the present disclosure are merely intended to describe specific embodiments, and are not intended to limit this application. The term "and/or" as used herein includes any and all combinations of one or more associated listed items.

Referring to FIGS. 1-7, an embodiment of the present disclosure provides a detector with a removable antenna, which includes: a detector body 10, a connecting piece 20, and an antenna 30. The detector body 10 includes a first connecting part 11. A signal receiving end 12 is arranged on the first connecting part 11. One end of the connecting piece 20 is detachably connected with the first connecting part 11. The antenna 30 includes a second connecting part 31. A signal output end 32 is arranged on the second connecting part 31. The other end of the connecting piece 20 is detachably connected with the second connecting part 31 so as to make the signal output end 32 in contact and electrically connected with the signal receiving end 12.

By arranging above structures, when in use, the first connecting part 11 and the second connecting part 31 can be respectively connected through the connecting piece 20. At this time, the signal output end 32 and the signal receiving end 12 are in contact and electrically connected, making it convenient to connect the detector body 10 and the antenna 30 or detach the antenna 30 from the detector body 10. It is convenient to use and convenient for storage and carrying.

In this embodiment, the second connecting part 31 comprises a sliding rod 311 and a protruding structure 312 protruding from a surface of the sliding rod 311. The connecting piece 20 defines a sliding hole 21, and an inner wall surrounding the sliding hole 21 is provided with a blocking protrusion 22. When the sliding rod 311 is inserted into the sliding hole 21, and the protruding structure 312 resists against the blocking protrusion 22. By setting the above structure, the sliding rod 311 is inserted into the sliding hole 21, allowing the connecting piece 20 to slide or rotate on the sliding rod 311 which facilitate a user operating on the connecting piece 20 to make the first end of the connecting piece 20 connected to the first connecting part 11. The protruding structure 312 resists against the blocking protrusion 22, which can prevent the connecting piece 20 from detaching from the second connecting part 31 along an axis direction of the sliding rod 311, ensuring stability of a connection between the second connecting part 31 and the second end of the connecting piece 20.

In the embodiment, the detector further includes a sealing ring 40 sleeved on the sliding rod 311 and clamped between the protruding structure 312 and the blocking protrusion 22.

By arranging such structures, the sealing ring 40 ensures the seal between the second connecting part 31 and the connecting piece 20, prevents debris from entering the connecting piece 20 through a gap between the sliding rod 311 and the inner wall surrounding the sliding hole 21, thus ensuring stability of the signal output end 32 and the signal receiving end 12. The sealing ring 40 is elastic, clamping it between the protruding structure 312 and the blocking protrusion 22 can provide buffering and prevent the protruding structure 312 and the blocking protrusion 22 from being damaged due to long-term direct contact.

In the embodiment, the connecting piece 20 is provided with a connection groove 23 communicated with the sliding hole 21, and the first connecting part 11 is configured to be inserted into the connection groove 23 to allow the signal output end 32 to contact and be electrically connected to the signal receiving end 12. By arranging such structures, the first connecting part 11 is inserted into the connection groove 23, which can prevent shaking after the first connecting part 11 is connected to the connecting piece 20, ensuring connection stability. The connection groove 23 can accommodate the signal output end 32 and the signal receiving end 12, thus protecting the signal output end 32 and the signal receiving end 12 and improving use safety.

In the embodiment, an inner wall surrounding the connection groove 23 is provided with a first connecting thread 231, the first connecting part 11 is provided with a second connecting thread 111, and the first connecting thread 231 is threaded to the second connecting thread 111. By arranging such structures, when in use, the first connecting part 11 is inserted into the connection groove 23, and the connecting piece 20 is rotated at the same time to make the first connecting thread 231 threaded with the second connecting thread 111, which is simpler and more convenient. At the same time, the threaded connection further improves connection stability.

In the embodiment, the signal output end 32 is provided with a first electrical contact in a shape of a concentric circular ring, and the signal receiving end 12 is provided with a second electrical contact corresponding to the first electrical contact. When the signal output end 32 is electrically connected with the signal receiving end 12, the first electrical contact is electrically connected to the second electrical contact. By such arrangement, the first and second electrical contacts are in a shape of the concentric circular ring, which is convenient for a user to connect the first electrical contact with the second electrical contact, without a need to manually align a socket or probe on the first electrical contact and a probe or socket on the second electrical contact to achieve an electrical connection between the first and second electrical contacts, making installation more convenient and efficient.

In the embodiment, the detector body 10 is equipped with a handle 13, which is configured for users to hold and use. By such arrangement, the handle 13 can facilitate the user to hold the detector body 10, thereby facilitating the user to find the position of the signal transmission device and making it more convenient to use.

In the embodiment, the handle 13 is equipped with an uneven grip portion 131, which is used to fit the user's finger portion. When in use, the user's fingers are pressed against the uneven grip portion 131 to enhance stability of the user's grip on the handle and prevent the detector from falling off.

In the embodiment, the detector body 10 is equipped with a control board 50, and the signal receiving end 12 is electrically connected to the control board 50. The control board 50 is configured to receive a signal transmitted by the signal receiving end 12. The control board 50 can receive and process signals transmitted by the signal receiving end 12, and output different sounds, images, etc., making it convenient for users to quickly find the position of the signal transmission device, based on this, making it more convenient to use.

In the embodiment, the detector body 10 is equipped with a battery 60, which is electrically connected to and supplies power to the control board 50. The arrangement of the battery 60 improves the battery life of the detector and allows it to be used without mains power, making the product more diverse in usage scenarios and eliminating inconvenience caused by insufficient wire length for users. Preferably, the battery 60 is either a built-in battery or a detachable battery.

In the embodiment, an upper surface of the detector body 10 is equipped with a pointer meter 70, which is electrically connected to the control board 50. The control board 50 controls rotation of the pointer meter 70 based on the signal transmitted by the signal receiving end 12. By such arrangement, the control board 50 controls the pointer meter 70 to rotate based on the signal transmitted by the signal receiving end 12. Users can intuitively understand a strength of the signal through the position of the pointer, and quickly find the strongest point of the signal based on the strength of the signal, thereby finding the position of the signal transmission device, which is more convenient to use.

In the embodiment, the upper surface of the detector body 10 is equipped with an indicator light 51, which is electrically connected to the battery 60. The indicator light 51 is used to indicate remaining capacity of the battery 60. By such arrangement, users can use the indicator light 51 to intuitively understand the remaining capacity of battery 60, which is helpful for understanding of the battery life. This facilitates timely charging or battery replacement, improving user experience.

In the embodiment, the upper surface of the detector body 10 is equipped with a switch 52, which is electrically connected to the control board 50. The switch 52 is configured to turn on or off the circuit. The switch 52 can facilitate users to turn on or off the detector body 10, thus saving power when not in use.

In the embodiment, the detector body 10 is equipped with a sound playback device 80, which is electrically connected to the control board 50. The control board 50 controls the sound playback device 80 to play sound based on the signal transmitted by the signal receiving end 12. By such arrangement, the control board 50 controls the sound playback device 80 to play sound based on the signal transmitted by the signal receiving end 12. For example, by distinguishing different signal strengths based on sound size and frequency, users can roughly judge the distance between the sound and the signal transmission device by listening to the sound, further facilitating user use.

In the embodiment, the upper surface of the detector body 10 is equipped with a sound through-hole 14, which corresponds to the sound playback device 80. By such arrangement, the sound through-hole 14 can allow sound waves to pass therethrough, allowing users to hear the sound generated by the sound playback device 80 more clearly.

In the embodiment, the detector further includes an adjustment switch 53, which is electrically connected to the control board 50. The adjustment switch 53 is configured for users to switch the signal frequency that can be detected by the antenna 30. The adjusting switch 53 can adjust the signal frequency that antenna 30 can detect, improving adaptability of the detector.

In the embodiment, the detector further includes a protective sleeve 33, which is set at the end of the antenna 30. By such arrangement, the protective sleeve 33 can protect the antenna 30 and prolong a service life of the detector.

Figure 1:
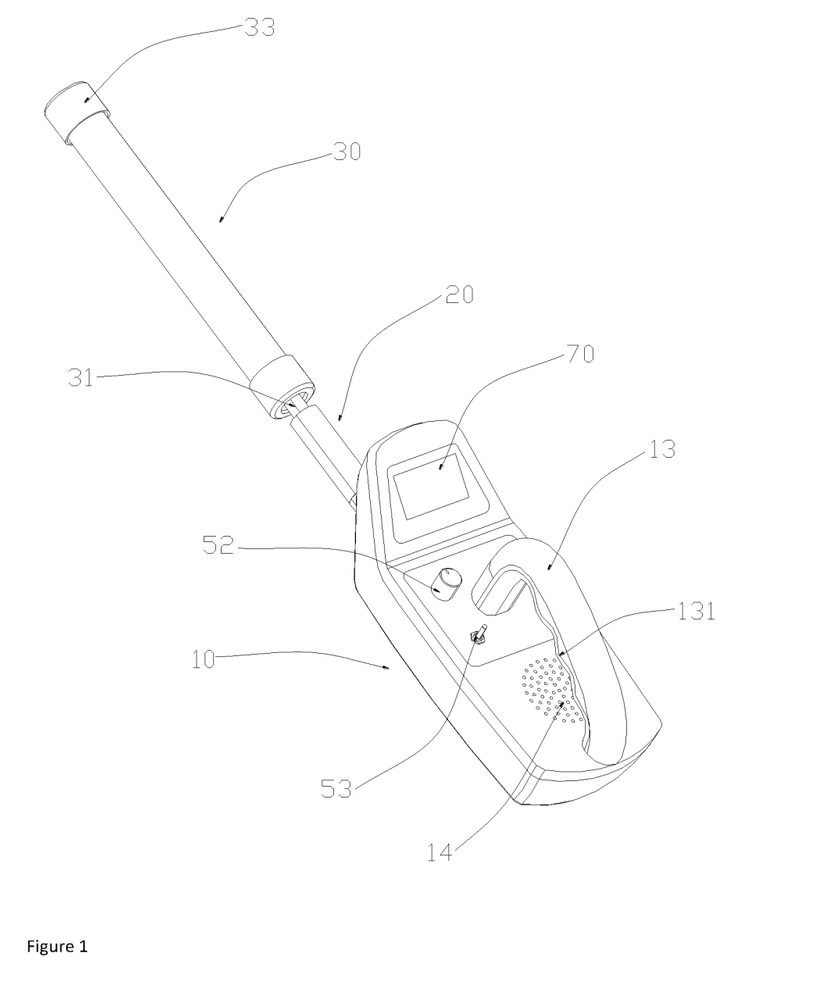
FIG. 1 is a schematic structural diagram of a detector with a detachable antenna taken from a first view according to a first embodiment of the present disclosure.
Figure 2:
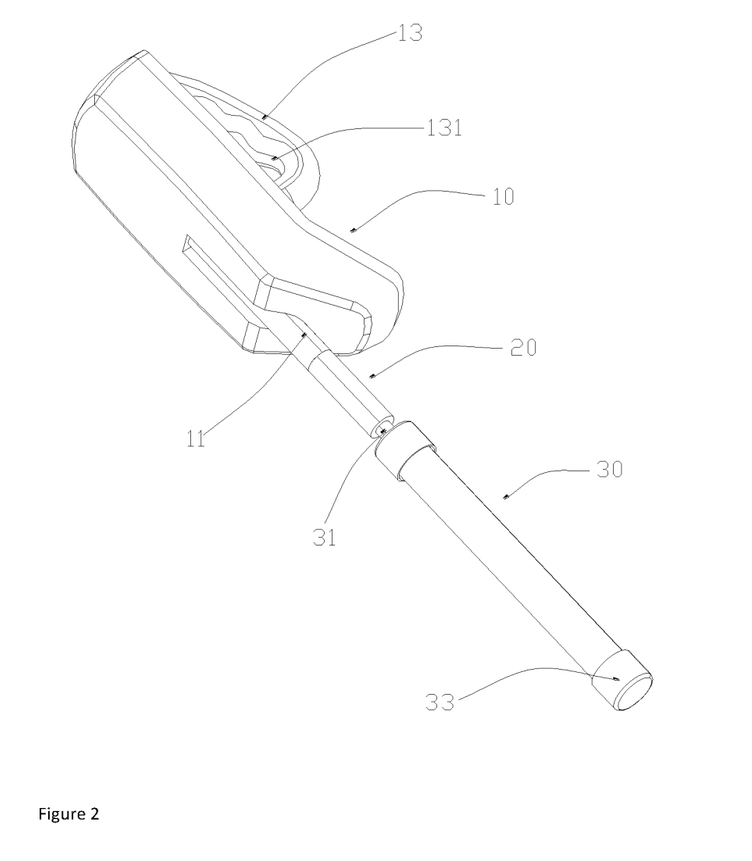
FIG. 2 is a schematic structural diagram of the detector with a detachable antenna of FIG. 1 taken from a second view.
Figure 3:
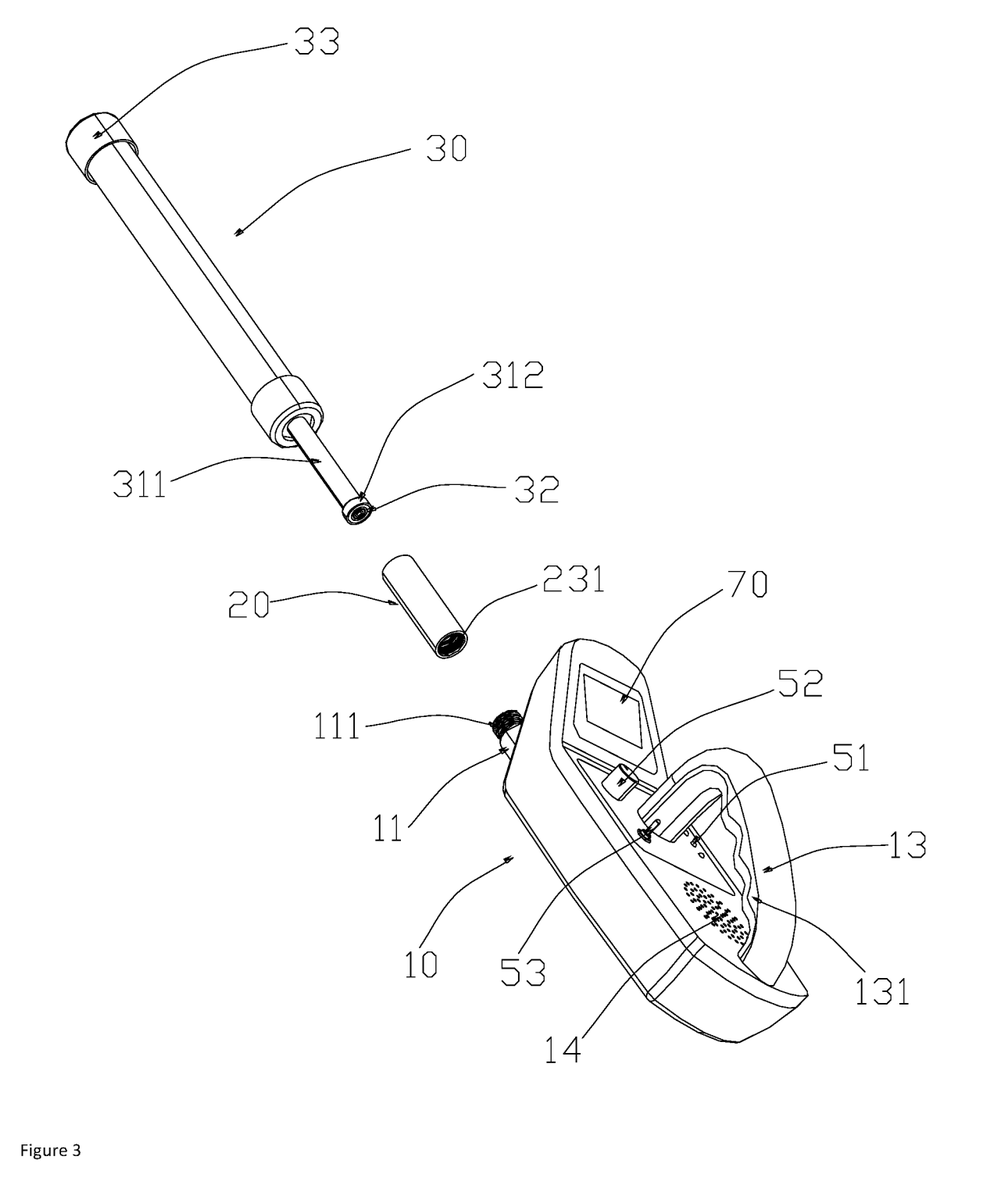
FIG. 3 is an exploded view of the detector with the detachable antenna of FIG. 1 taken from a first view.
Figure 4:
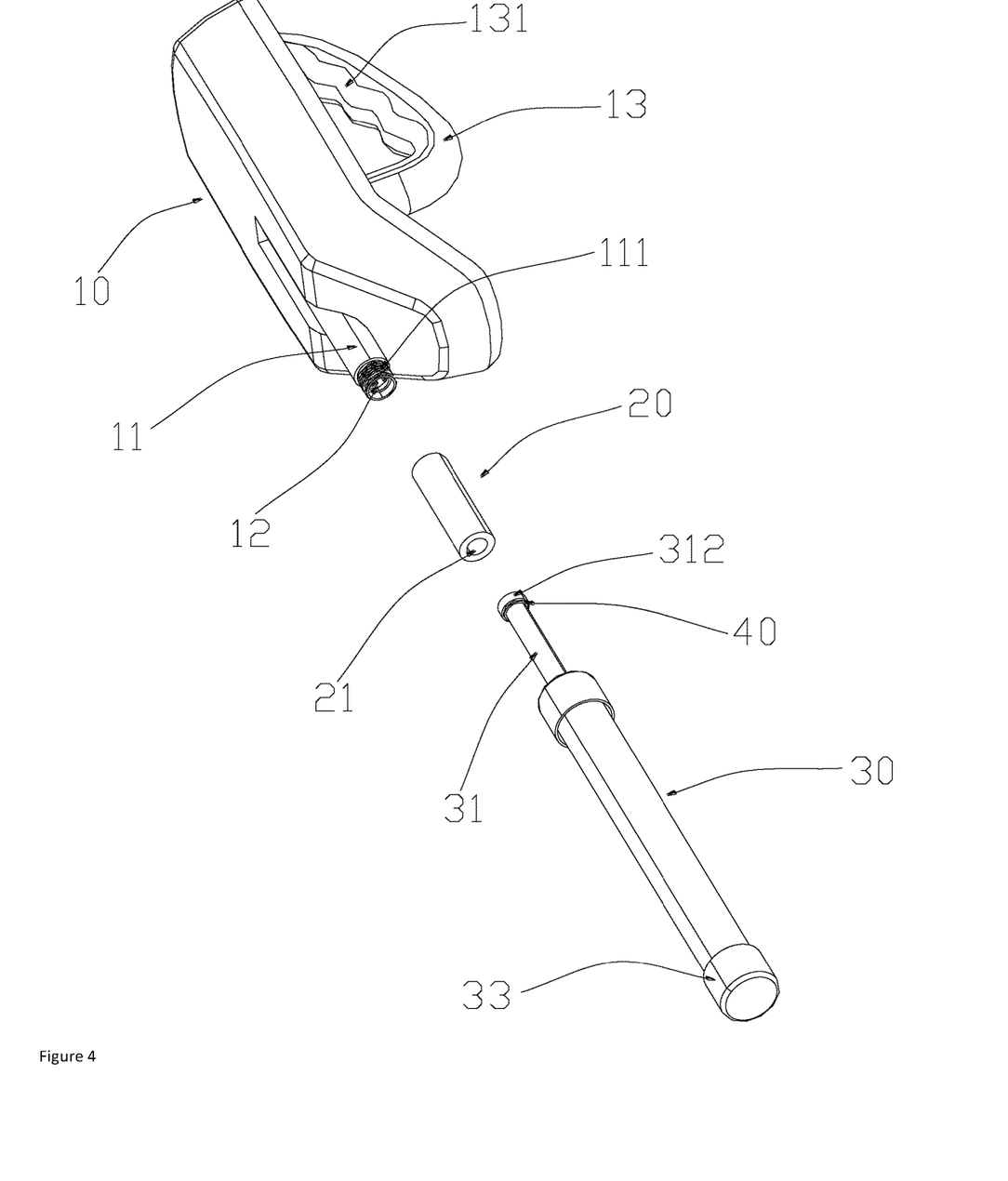
FIG. 4 is an exploded view of the detector with the detachable antenna of FIG. 1 taken from a second view.
Figure 5:
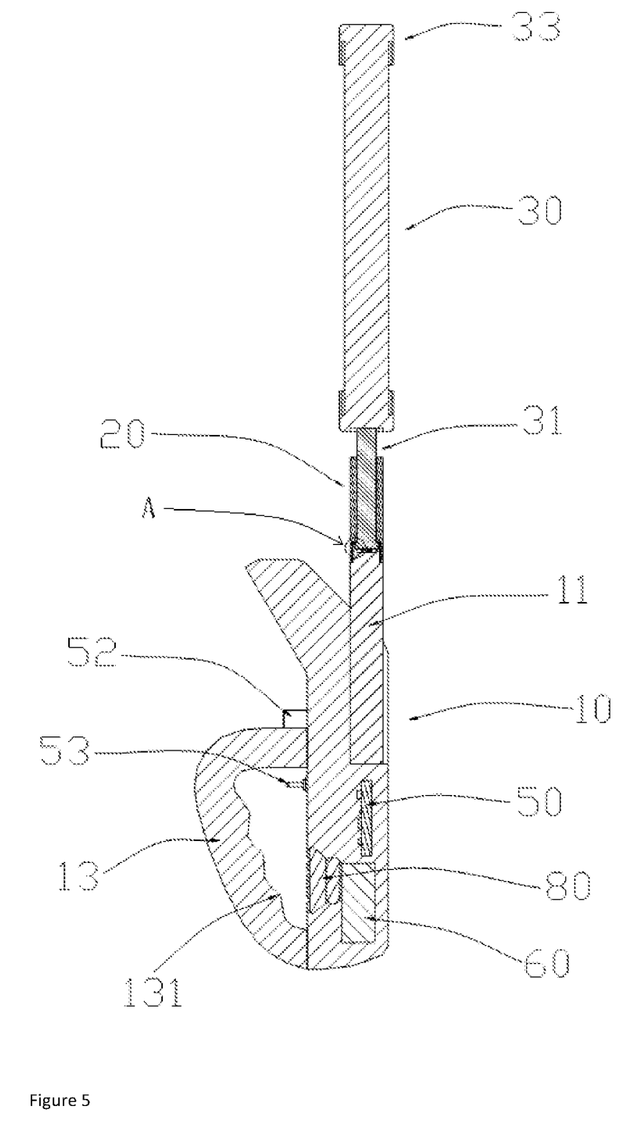
FIG. 5 is a sectional view of the detector with the detachable antenna of FIG. 1
Figure 6:
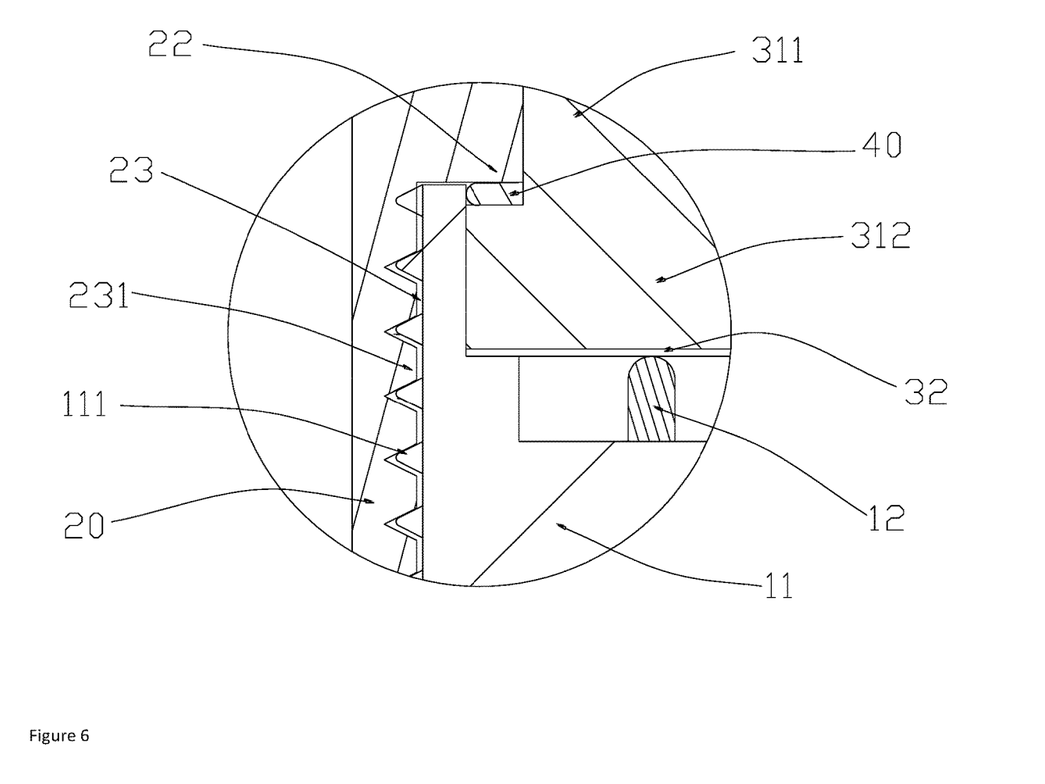
FIG. 6 is an enlarged view of the portion A shown in FIG. 5.
Figure 7:
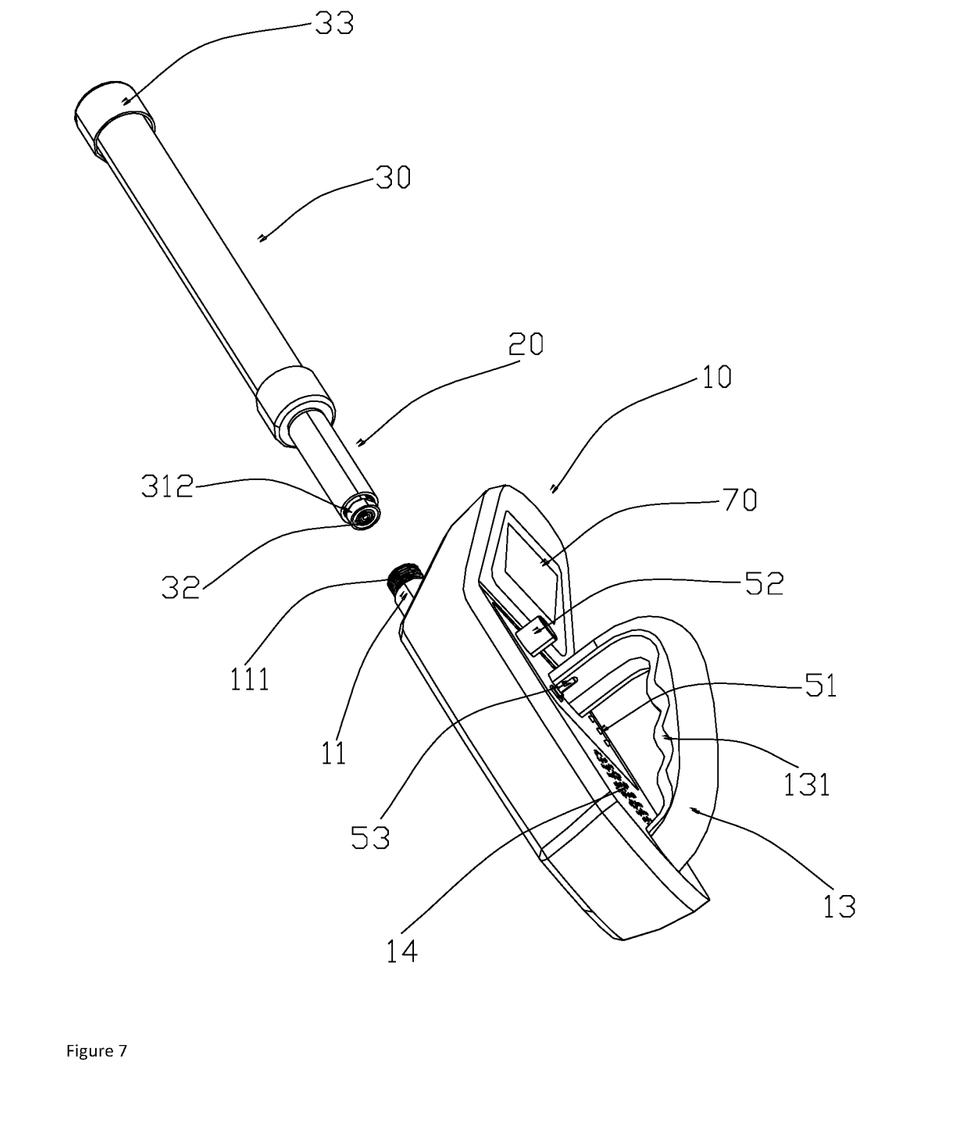
FIG. 7 is a a schematic structural view of the detector with the detachable antenna of FIG. 1 with the antenna being detached.
Figure 8:
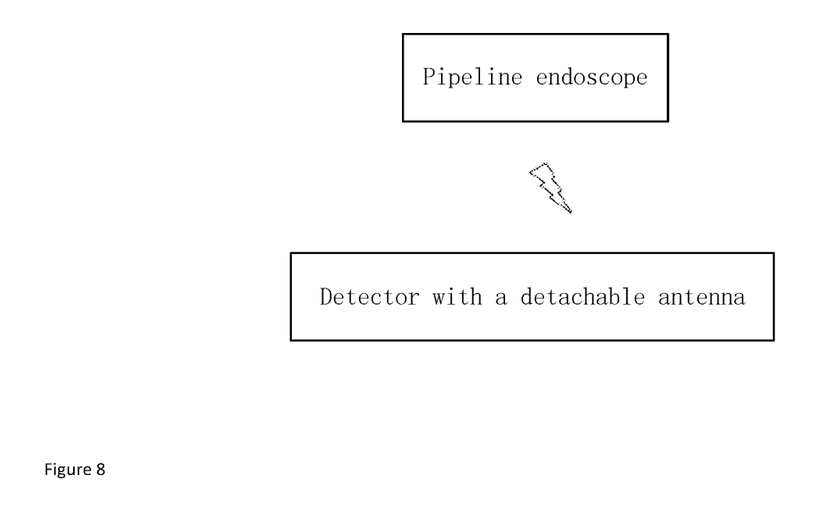
FIG. 8 is a block diagram of a detector assembly according to an embodiment of the present disclosure.

Please refer to FIG. 8. An embodiment of the present disclosure provides a detector assembly, which includes the detector with the detachable antenna as shown in FIGS. 1-7 and a pipeline endoscope. Specifically, the detector with the detachable antenna may have a signal receiver, and the pipeline endoscope may have a signal transmitter, allowing the detector with the detachable antenna to detect the position and status of the pipeline endoscope through wireless signals.

The technical features in the foregoing embodiments may be combined in any manner. To make the description brief, all possible combinations of the technical features in the foregoing embodiments are not described. However, as long as there is no contradiction between the combinations of the technical features, it should be considered as the scope described in this specification. The foregoing embodiments represent only several embodiments of the present disclosure, and descriptions thereof are relatively specific and detailed, but may not be construed as a limitation on the scope of the present disclosure. It should be noted that an ordinary person skilled in the art may make some modifications and improvements without departing from the concept of the present application, which are within the protection scope of the present application.

The invention claimed is:

1. A detector with a detachable antenna, comprising:
a detector body, has a first connecting part, wherein the first connecting part is equipped with a signal receiving end;
a connecting piece, wherein the first end of the connecting piece is detachably connected to the first connecting part; and
antenna, wherein the antenna is provided with a second connecting part, wherein the second connecting part is provided with a signal output end, and the second end of the connecting piece is detachably connected to the second connecting part to make the signal output end contact and electrically connected to the signal receiving end.

2. The detector with a detachable antenna according to claim 1, wherein the second connecting part comprises a sliding rod and a protruding structure protruding from a surface of the sliding rod, the connecting piece is provided with a sliding hole, an inner wall surrounding the sliding hole is provided with an blocking protrusion, and when the sliding rod is inserted into the sliding hole the protruding structure resists against the blocking protrusion.

3. The detector with a detachable antenna according to claim 2, further comprising a sealing ring, wherein the sealing ring is sleeved on the sliding rod and clamped between the protruding structure and the blocking protrusion.

4. The detector with a detachable antenna according to claim 2, wherein the connecting piece is provided with a connecting groove communicated with the sliding hole, and the first connecting part is configured to be inserted into the connecting groove to have the signal output end to contact and be electrically connected to the signal receiving end.

5. The detector with a detachable antenna according to claim 4, wherein an inner wall surrounding the connecting groove is provided with a first connecting thread, the first connecting part is provided with a second connecting thread, and the first connecting thread is configured to be threaded to the second connecting thread.

6. The detector with a detachable antenna according to claim 1, wherein the signal output end is provided with a first electrical contact of a concentric circular shape, the signal receiving end is provided with a second electrical contact corresponding to the first electrical contact, and the first electrical contact is configured to be electrically connected to the second electrical contact.

7. The detector with a detachable antenna according to claim 1, wherein a handle is provided on the detector body for a user to grip and use.

8. The detector with a detachable antenna according to claim 7, wherein the handle is provided with an uneven grip portion, which is used to fit the user's finger portion.

9. The detector with a detachable antenna according to claim 1, wherein a control board is provided inside the detector body, and the signal receiving end is electrically connected to the control board, and the control board receives a signal transmitted by the signal receiving end.

10. The detector with a detachable antenna according to claim 9, wherein a battery is provided inside the detector body, and the battery is electrically connected to and supplies power to the control board.

11. The detector with a detachable antenna according to claim 9, wherein a pointer meter is provided on an upper surface of the detector body and Is electrically connected to the control board, the control board controls rotation of a pointer of the pointer meter based on the signal transmitted by the signal receiving end.

12. The detector with a detachable antenna according to claim 10, wherein an indicator light is provided on an upper surface of the detector body and is electrically connected to the battery, and the indicator light is configured to indicate remaining capacity of the battery.

13. The detector with a detachable antenna according to claim 9, wherein a switch is provided on a surface of the detector body and is electrically connected to the control board and configured to turn on or off the detector.

14. The detector with a detachable antenna according to claim 9, wherein the detector body is equipped with a sound playback device electrically connected to the control board, the control board controls the sound playback device to play sound based on the signal transmitted by the signal receiving end.

15. The detector with a detachable antenna according to claim 14, wherein an upper surface of the detector body is provided with a sound through-hole corresponding to the sound playback device.

16. The detector with a detachable antenna according to claim 9, further comprising an adjustment switch electrically connected to the control board, and the adjustment switch is configured for the user to switch a signal frequency that the antenna can detect.

17. The detector of the detachable antenna according to claim 1, further comprising a protective sleeve arranged at an end of the antenna.

18. A detector assembly, comprising a detector with a detachable antenna and a pipeline endoscope, wherein the detector with a detachable antenna is configured to detect the pipeline endoscope, the detector with a detachable antenna comprising:
a detector body, has a first connecting part, wherein the first connecting part is equipped with a signal receiving end;

a connecting piece, wherein the first end of the connecting piece is detachably connected to the first connecting part; and antenna, wherein the antenna is provided with a second connecting part, wherein the second connecting part is provided with a signal output end, and the second end of the connecting piece is detachably connected to the second connecting part to make the signal output end contact and electrically connected to the signal receiving end.

* * * * *